United States Patent
Venturelli (10) Patent No.: US 7,846,128 B2
(45) Date of Patent: Dec. 7, 2010

(54) CATHETER AND METHOD FOR MAKING SAME

(75) Inventor: Andrea Venturelli, Brescia (IT)

(73) Assignee: Invatec S.r.l., Roncadelle (Brescia) (IT)

( * ) Notice: Subject to any disclaimer, the term of this patent is extended or adjusted under 35 U.S.C. 154(b) by 262 days.

(21) Appl. No.: 11/568,670

(22) PCT Filed: May 5, 2004

(86) PCT No.: PCT/IT2004/000248
§ 371 (c)(1), (2), (4) Date: Jan. 23, 2007

(87) PCT Pub. No.: WO2005/105192
PCT Pub. Date: Nov. 10, 2005

(65) Prior Publication Data
US 2007/0270780 A1    Nov. 22, 2007

(51) Int. Cl.
*A61M 29/00* (2006.01)
*A61M 31/00* (2006.01)
*A61M 25/00* (2006.01)
*A61B 17/28* (2006.01)

(52) U.S. Cl. .................. 604/96.01; 604/523; 604/508; 606/213

(58) Field of Classification Search .................. 604/19, 604/20, 265; 424/443; 514/12, 772; 600/466
See application file for complete search history.

(56) References Cited

U.S. PATENT DOCUMENTS

| | | | | |
|---|---|---|---|---|
| 4,681,110 A * | 7/1987 | Wiktor | ...... | 606/194 |
| 5,244,619 A * | 9/1993 | Burnham | ...... | 264/171.2 |
| 5,401,257 A | 3/1995 | Chevalier, Jr. et al. | | |
| 5,769,819 A * | 6/1998 | Schwab et al. | ...... | 604/103 |
| 5,911,715 A * | 6/1999 | Berg et al. | ...... | 604/525 |
| 6,110,191 A * | 8/2000 | Dehdashtian et al. | ...... | 606/192 |
| 6,322,586 B1 * | 11/2001 | Monroe et al. | ...... | 623/1.11 |
| 6,503,353 B1 * | 1/2003 | Peterson et al. | ...... | 156/86 |
| 6,790,221 B2 * | 9/2004 | Monroe et al. | ...... | 623/1.11 |
| 2002/0052641 A1 * | 5/2002 | Monroe et al. | ...... | 623/1.11 |

FOREIGN PATENT DOCUMENTS

EP    1199051    4/2002

* cited by examiner

Primary Examiner—Nicholas D Lucchesi
Assistant Examiner—Ian K Holloway
(74) Attorney, Agent, or Firm—Shoemaker and Mattare (57) ABSTRACT

The present invention relates to a catheter, its proximal portion and the tip thereof as well as to the method for making the same. The distal flap of the catheter main tube comprises a plurality of reliefs arranged on planes transversal to the tube axis; a tapered portion coaxially connected to the distal flap comprising a plurality of notches complementary to said reliefs.

34 Claims, 10 Drawing Sheets

CATHETER AND METHOD FOR MAKING SAME

FIELD OF THE INVENTION

The present invention relates to a catheter for endoluminal operations, the distal section and the tip thereof. The methods for making both the distal section and catheter tip are also parts of the present invention.

The present invention is directed to improve the characteristics of a catheter suitable to carry out endoluminal operations on a living body, particularly suitable to position a self-expandable stent, in order to restore the original section of a blood vessel prone to stenosis.

BACKGROUND OF THE INVENTION

In case of endoluminal operations two contrasting needs are felt for catheters: great axial compression stiffness but also great flexibility. The axial compression stiffness allows the catheter distal section to be readily responsive to the movements caused on the proximal section by the operator. On the other hand, the flexibility allows the catheter to find its way through the blood vessels, which is often a tortuous path, in the simplest and less traumatic way for the patient.

This need for flexibility is particularly felt for the catheter distal section which is intended to reach those vessels which, among those being run through by the catheter, are of a smaller diameter.

For the same reasons, this need for flexibility is even more felt for the catheter tip.

Another requirement for the catheter tip is to fair the front profile of the catheter from its minimum diameter, such as that of the lumen with a guide wire running therein, to its maximum diameter available in the distal section, such as that of a sheath holding a stent in its state of maximum radial collapse.

A further requirement for the catheter tip is to ensure that the flexibility of the distal end in the proximal direction will change as evenly as possible.

A still further need for both the catheter and its tip is to ensure their mutual adherence, also in most severe usage conditions, in order to prevent any disjunction between the catheter main body and its tip.

Catheter tips are known to be added to the catheter main body by overmoulding. These known tips are obtained by means of a mould reproducing their shape, inside which the distal end of the tube being the catheter main body is inserted. A plastic material is then injected into the mould. While polymerizing, it adheres to the outer surface of the catheter main body.

The above catheter tips are known to have poor flexibility which abruptly changes at the point where, inside the tip, the tube being the catheter main body ends.

Due to its almost mere chemical nature, the adherence of these tips to the catheter main bodies is also known to be negatively affected, and in some cases even impaired, by a non-optimum preparation of the respective polymeric materials.

OBJECTS AND SUMMARY OF THE INVENTION

From what has been discussed above, it emerges how felt is the need to have a catheter being able to ensure the optimum flexibility above all in the distal section thereof, gradual variation of this flexibility and safe adherence of the tip to the catheter main body.

It is also understood that the need is felt to obtain such a catheter, the distal section and tip thereof by means of a simple method, which does not require expensive technologies and ensures an optimum result by limiting the risk of errors.

The problem at the heart of the present invention is to provide a catheter, a catheter distal section and tip having such structural and functional characteristics to overcome the above drawbacks mentioned with reference to the prior art.

A further object of the present invention is to conceive and provide a method for manufacturing these distal section and catheter tip, which method allows to meet the above requirements.

These problems are resolved by a catheter tip according to claim 1, a distal section according to claim 13, a catheter according to claim 17 and by the methods for manufacturing the catheter distal section according to claims 19 and 26, respectively.

BRIEF DESCRIPTION OF THE DRAWINGS

Further characteristics and the advantages of the catheter, catheter distal section and tip as well as the method for manufacturing the same according to the invention will appear from the herein description of some exemplary embodiments thereof, which are intended to be merely illustrative and non-limiting, with reference to the annexed figures, in which.

DESCRIPTION OF THE PREFERRED EMBODIMENTS

Figure 1A:
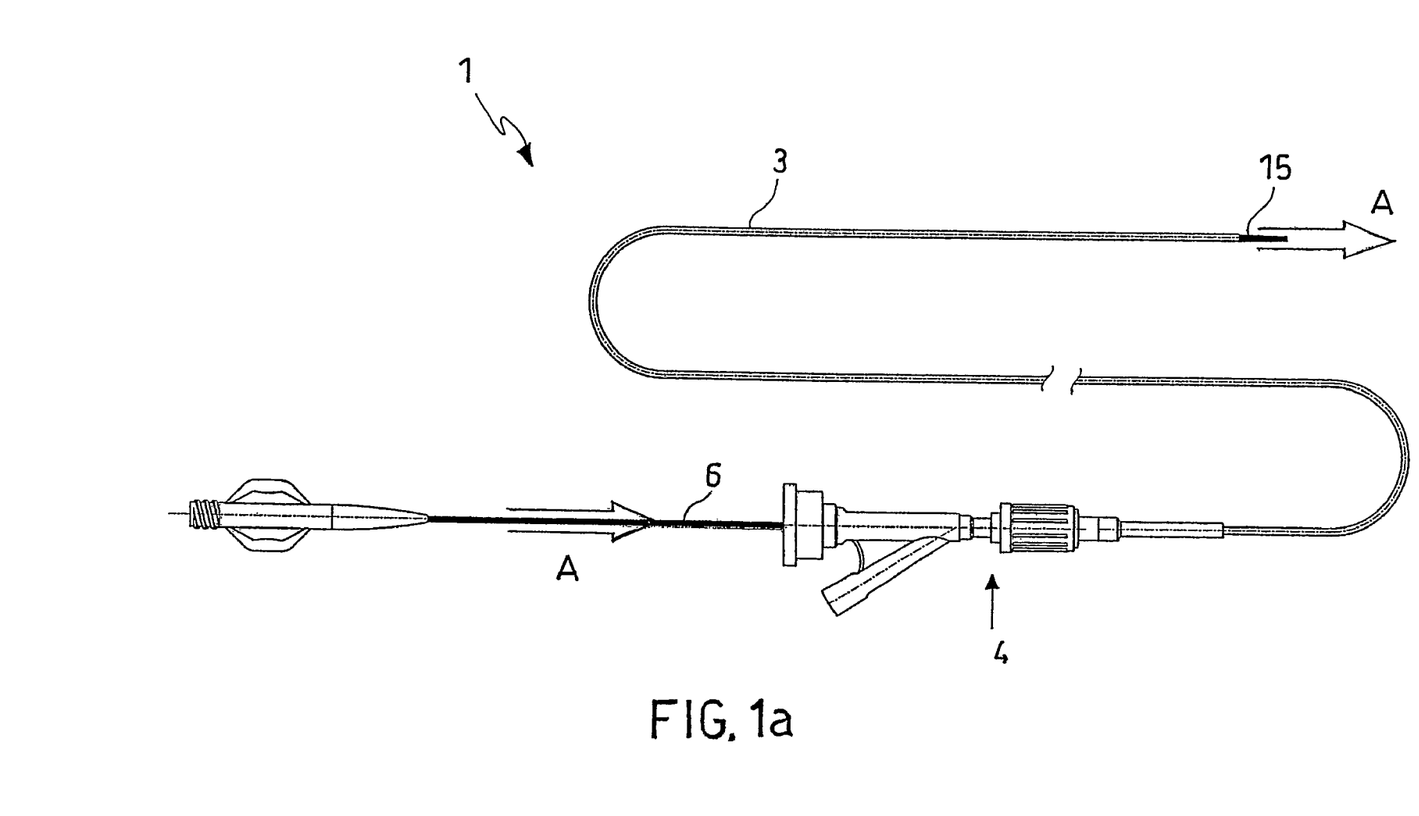
FIG. 1*a* shows an overall view of an embodiment of the catheter in a first configuration.
Figure 1B:
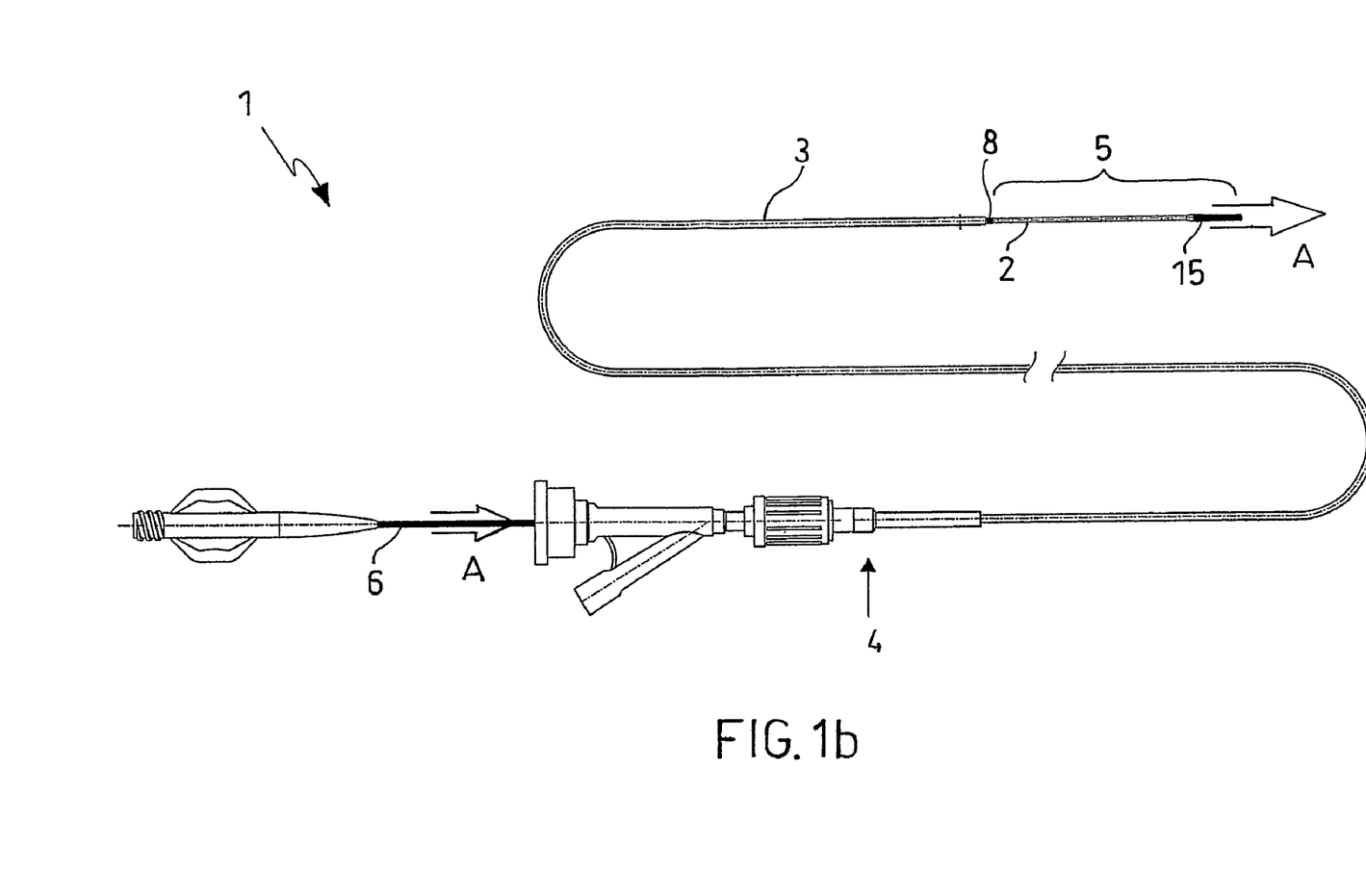
FIG. 1*b* shows the catheter from FIG. 1*a* in a second configuration.

With reference to said FIGS. 1*a* and 1*b*, with 1 has been indicated a catheter for endoluminal operations as a whole. The catheter illustrated by way of example consists of a main tube 2 and a sheath 3. The sheath 3 is arranged around the main tube 2.

In accordance with a preferred embodiment, an intermediate tube 23 being fitted on main tube 2 is coaxially interposed between the main tube 2 and the sheath 3. In accordance with an embodiment (FIG. 8*c*), the intermediate tube 23 is a polymeric tube, such as extruded.

In accordance with another preferred embodiment, the intermediate tube 23 comprises a reinforcement made of a material stiffer than the polymer composing the wall of the intermediate tube 23.

Figure 9A:
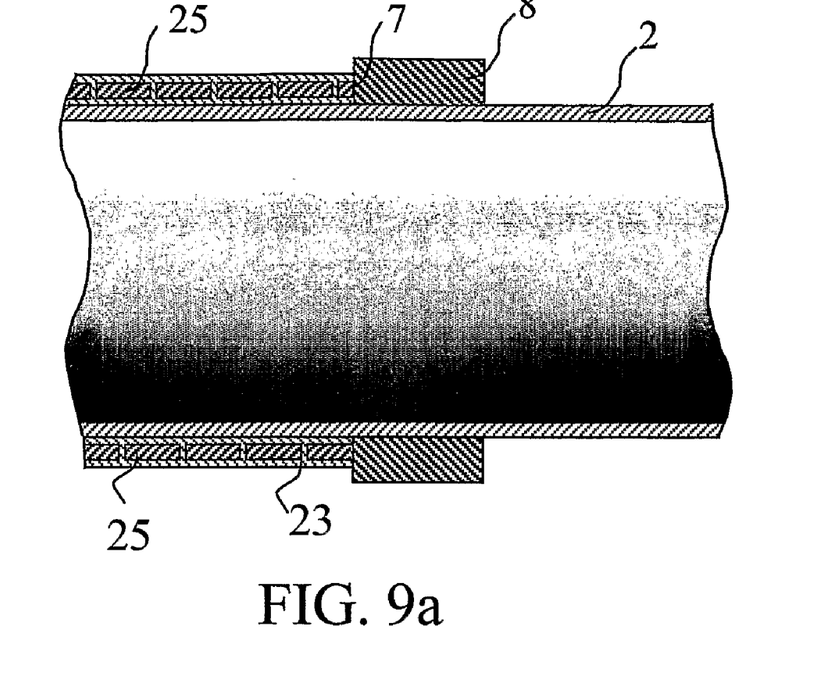
FIGS. 9*a* and 9*b* are schematic sectional views of a detail of the catheter according to two embodiments which are similar to that from FIG. 8*c*.

The intermediate tube 23 may for example comprise (FIG. 9a) a coil 25 obtained by winding a metal strip and drowning it inside the thickness of the wall.

Figure 9B:
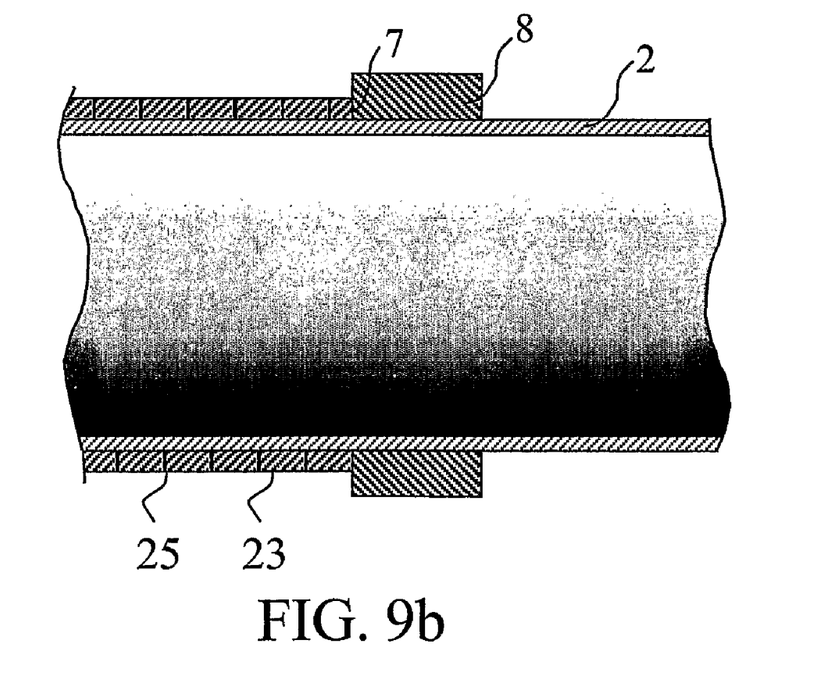

Alternatively, the coil 25 itself may be the intermediate tube 23 (FIG. 9b). In this case, in fact, the turns of coil 25 are in contact with one another and are themselves a substantially continuous wall, instead of being drowned therein.

The use of coil 25, either drowned in the tube wall or not, is a practical solution which is independent from the other characteristics described herein and may be also employed in catheters other than those described herein.

The inner diameter of sheath 3 is slightly greater than the outer diameter of either main tube 2 or, if provided, intermediate tube 23. The sheath 3 and the tube 2 can thus easily slide one onto the other. Particularly, arrows A in FIGS. 1a and 1b show which movements the main tube 2 and all the members integral therewith can make relative to sheath 3. The catheter can thus turn from a first configuration where sheath 3 covers substantially all the main tube 2 (FIG. 1a) to a second configuration where sheath 3 is withdrawn and leaves a distal section 5 of catheter 1 uncovered (FIG. 1b).

The intermediate tube 23 and/or the metal coil 25, if present, allows to greatly increase the catheter axial compression stiffness without impairing the flexibility thereof. Thereby, the action by the operator to force the catheter 1 along sheath 3 by means of rod 6 is simplified.

In a proximal section 4 of the embodiments illustrated in FIGS. 1a and 1b, main tube 2 is coaxially joint to a stiff rod 6. On the other hand, in distal portion 50, main tube 2 comprises a shoulder 7.

Figure 8A:
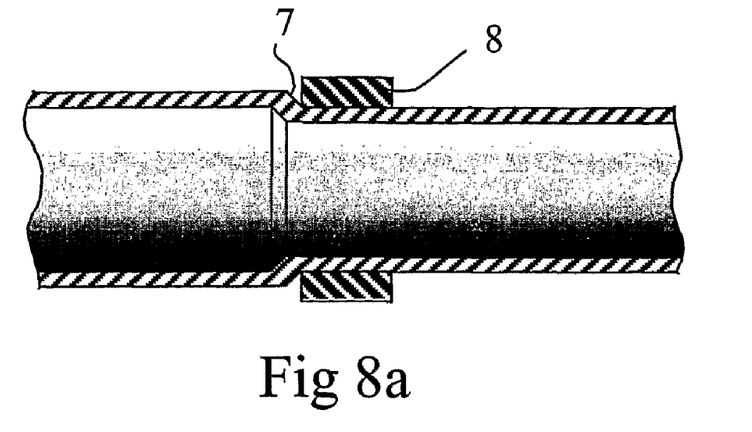
FIGS. 8*a*, 8*b* and 8*c* are schematic sectional views of a detail of the catheter according to three different embodiments according to the invention.
Figure 8B:
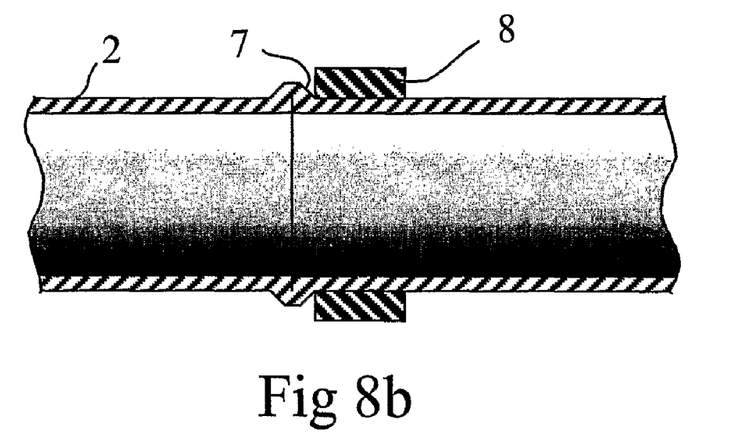

In accordance with an embodiment, this shoulder 7 originates from an abrupt change of the outer diameter of main tube 2 (FIGS. 8a and 8b).

Figure 8C:
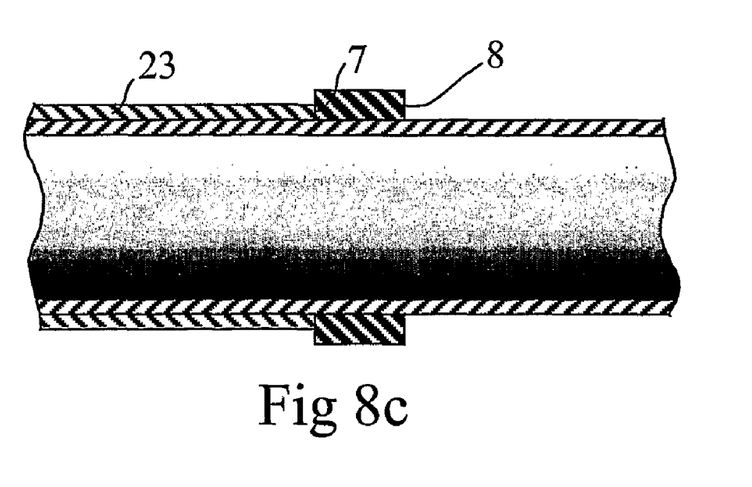

In accordance with another embodiment, the shoulder 7 originates from the distal end of the intermediate tube 23 (FIG. 8c).

In a preferred embodiment, a first radiopaque marker 7 is placed to abut against this shoulder 7. This marker 8 is shaped such as to define in turn a shoulder suitable to axially receive in abutment a further tubular body, such as a stent which can be loaded onto the catheter distal section.

Positioning marker 8 in abutment to shoulder 7 and the marker defining a further shoulder, such as for a stent to abut thereagainst, is a practical solution which is independent from the other characteristics described herein, and can be employed also in catheters other than those described herein.

Following the distal direction along main tube 2, at a distance from first marker 8 that will be defined below, there is preferably a second radiopaque marker 8.

Markers 8 and 9 are typically made in heavy metal such as Tantalum, and/or a metal alloy such as Platinum-Iridium. They can be in the form of a ring, belt, sleeve, wire winding or any form which proves to be effective in a particular usage condition.

The distance between markers 8 and 9 is preset based on the length of a stent loadable on catheter 1. These markers are in fact prearranged for the operator to get a radiological confirmation about the actual positioning of distal section 5 of catheter 1 and hence of the stent loadable thereon.

A distal flap 10 of main tube 2 comprises, on the outer surface thereof, a plurality of reliefs 11.

In accordance with an embodiment, each of these reliefs 11 defines a main development direction.

accordance with a preferred embodiment, the main development direction of these reliefs 11 is transverse to the tube axis.

In accordance with a still more preferred embodiment, the main development direction of reliefs 11 is perpendicular to the tube axis.

Around the distal flap 10, coaxially to main tube 2, there is a tapered portion 12 which is also tubular. On the inner diameter of the tapered portion 12 a plurality of notches 13 is formed complementary to reliefs 11.

The distal apex of tapered portion 12 defines an apex port 14 being an outlet for a lumen 16 suitable for a guide wire to pass therethrough. The diameters of apex port 14 and lumen 16 are slightly greater than the diameter of the guide wire, such as to allow them to mutually slide.

In accordance with a preferred embodiment, distal section 120 of tapered portion 12 substantially has the shape of a truncated cone, which is suitable to fair the diameter of apex port 14 to the outer diameter of sheath 3.

A proximal section 122 of tapered portion 12 is, for example, shaped such as to fair the greater diameter of distal section 120 to the outer diameter of main tube 2.

Figure 2:
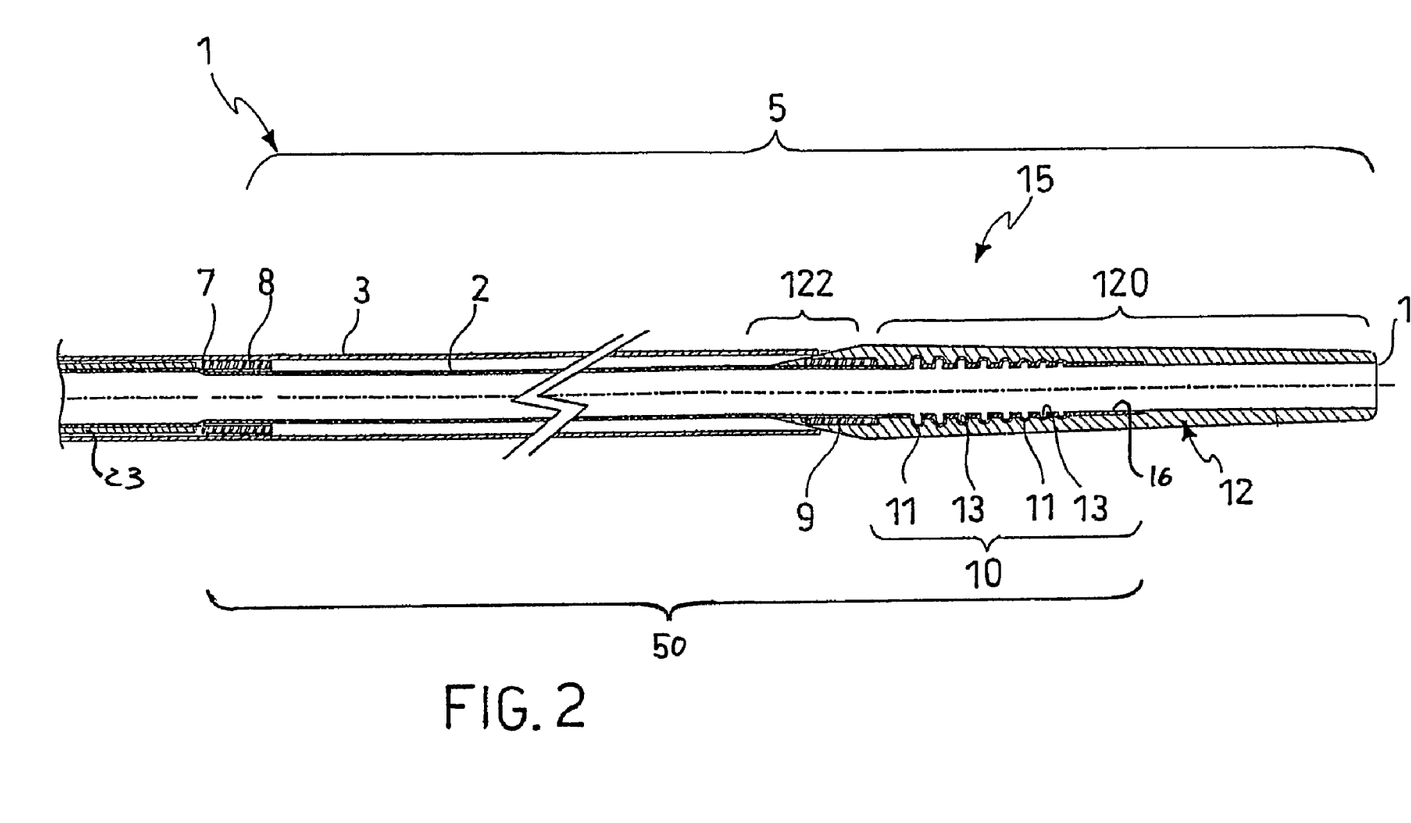
FIG. 2 shows the axially-sectioned detail of the distal section of the catheter from FIG. 1.

In accordance with certain embodiments, such as that illustrated in FIG. 2, proximal section 122 is of a regular shape, e.g. of a truncated cone.

Figure 3:
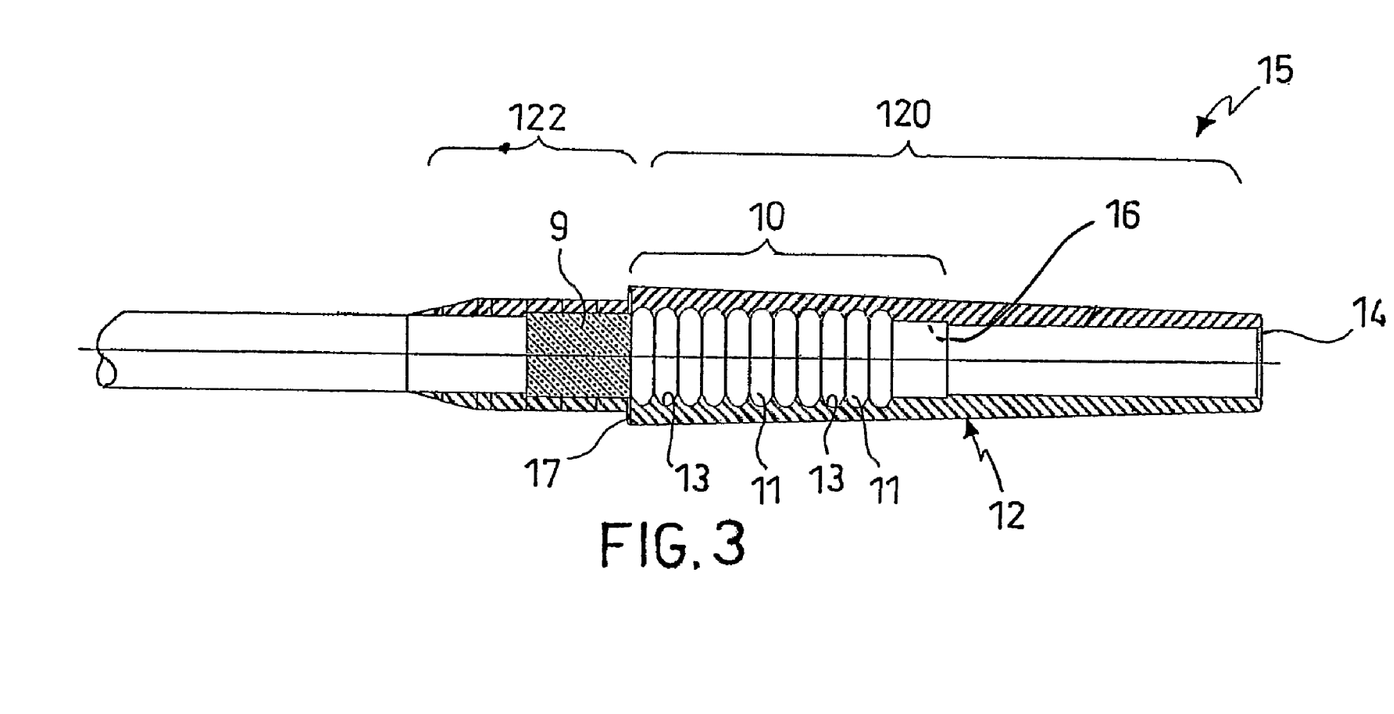
FIG. 3 shows a partially sectioned detailed view of a catheter tip according to another embodiment of the invention.

In accordance with other embodiments, such as that illustrated in FIG. 3, proximal section 122 also defines a second shoulder 17, suitable to axially receive in abutment either a further tubular body, such as sheath or a stent loadable on distal section 5 of the catheter.

Distal flap 10 and tapered portion 12 are comprised in a tip 15 of catheter 1. In the embodiments illustrated in the annexed figures, within tip 15 is also comprised second marker 9, housed in a suitable cavity formed in the proximal section 122 of tapered portion 12. In other embodiments, not illustrated, the second marker 9 may be not comprised within the tip 15 of catheter 1 or even not prearranged.

Methods for manufacturing the catheter distal section and the tip thereof according to the invention will be described below by means of some examples.

In accordance with a first embodiment, on a main tube 2 of the conventional type the first shoulder 7 is obtained by a partial drawing of distal portion 50 of main tube 2 itself.

In detail, the method provides that, for example, a first rigid stylet 19a the outer diameter of which is slightly smaller than the inner diameter of lumen 16 is inserted in the distal length of lumen 16 of main tube 2.

For example, with a 1 mm-inner diameter lumen 16, the outer diameter of first stylet 19a can be about 0.96 mm.

Figure 4A:
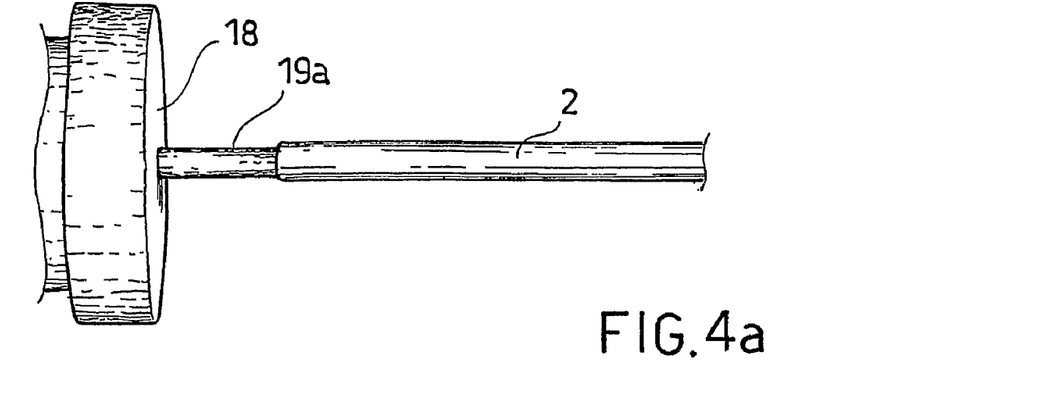
FIGS. 4*a*, 4*b* and 4*c* are schematic views of three sequential steps of an embodiment of the method according to the invention.
Figure 4B:
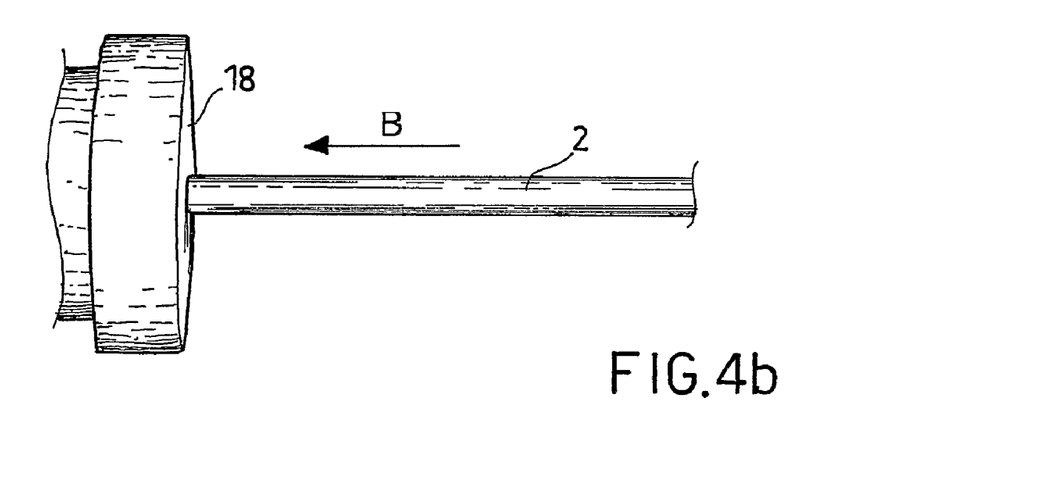
Figure 4C:
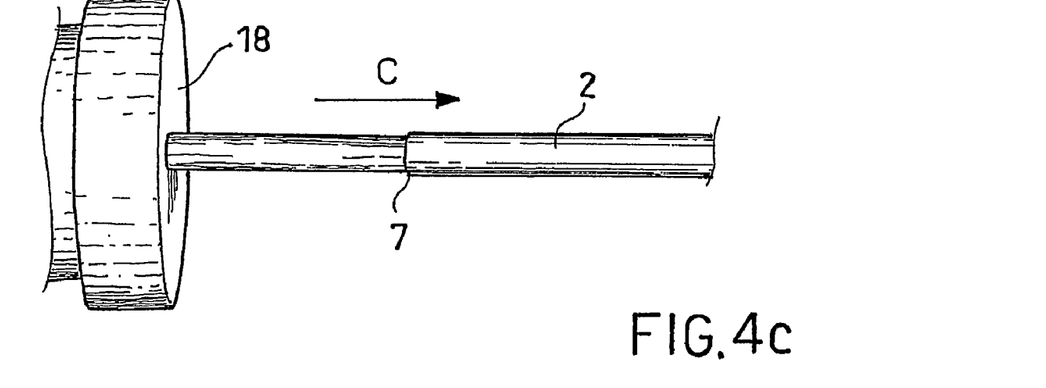

By inserting the rigid stylet 19a and prearranging a longitudinal notch acting as a runner, the distal portion 50 of tube 2 can be forced (arrow B in FIG. 4b) inside a first heated ferrule 18 with a slightly smaller diameter than the outer diameter of main tube 2. Accordingly, by hot plastic deformation a shrinkage of the main tube outer diameter is obtained all along the extension of the distal portion 50 which has been introduced in the first heated ferrule 18. By ending the drawing operation at the desired distance from the end of tube 2 and removing (arrow C in FIG. 4c) the tube from ferrule 18, an abrupt change of the tube outer diameter is obtained thus forming the shoulder 7 (FIG. 8a).

As an example, main tube 2 can be considered as being made of poly-ether ether ketone (PEEK) and with an outer diameter of 1.23 mm. In this case the first drawing ferrule 18 can have an inner diameter of 1.1 mm and be heated up to a temperature of around 180° C. Accordingly, a shrinkage of the outer diameter is obtained on main tube 2 from 1.23 mm to 1.1 mm, such as to define a shoulder 7 of about 0.065 mm.

In accordance with a second embodiment, on a main tube 2 of the conventional type a first shoulder 7 is obtained by making a relief on the wall of tube 2 (FIG. 8*b*). A method for making this relief is described in detail below.

In accordance with a third embodiment, on a main tube 2 of the conventional type a first shoulder 7 is obtained by interrupting the intermediate tube 23 (FIG. 8*c*).

In accordance with a preferred embodiment of the method, regardless of how it has been obtained, a first radiopaque marker 7 is approached to shoulder 7. The marker, as said above, can be made of a heavy metal such as Tantalum, and/or a metal alloy such as Platinum-Iridium. It can be in the form of a ring, a belt, a sleeve, a wire winding or any other form which proves effective in relation with the particular usage conditions.

In a preferred embodiment, the first marker 8 is prearranged in the form of a sleeve with an inner diameter equal to the outer diameter of main tube 2 or the drawn section thereof, and with an outer diameter slightly smaller than the inner diameter of sheath 3.

Figure 5A:
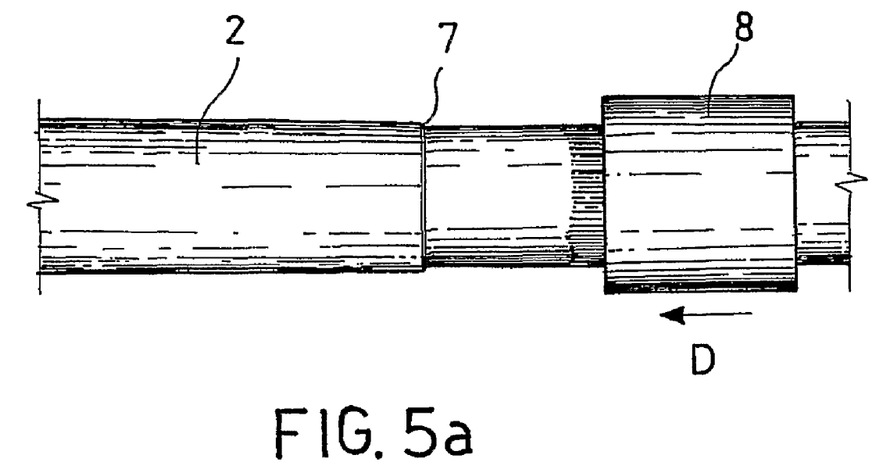
FIGS. 5*a* and 5*b* are schematic views of two sequential steps of an embodiment of the method according to the invention.
Figure 5B:
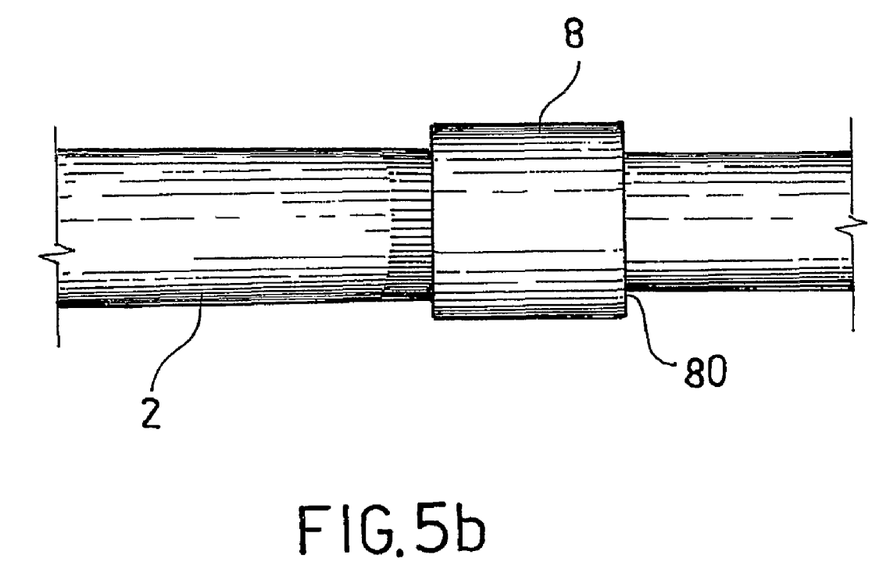

This first marker 8, is fit on the catheter distal section and is caused to slide (arrow D in FIG. 5*a*) in the proximal direction to axial abutment against the shoulder 7. In accordance with an embodiment of the method, marker 8 is fixed in this position, such as by a glueing 80, to prevent it from moving in the distal direction.

The method then provides to fit also second marker 9 onto the distal section of main tube 2. Preferably, this marker will have similar characteristics as the first marker 8. The second marker 9 is to be then secured to main tube 2, such as by glueing. The distance between first marker 8 and second marker 9 depends on the length of the stent to be loaded onto the distal section 5 of the catheter.

In accordance with an embodiment of the method, it is preferred to support the distal flap 10 of main tube 2 by inserting into the lumen 16 a second rigid stylet 19*b*. It is more preferred that the outer diameter of this stylet 19*b* is smaller than the diameter of lumen 16 and the outer diameter of first stylet 19*a*. For example, with a lumen 16 with an inner diameter of 1 mm, the outer diameter of second stylet 19*b* can be about 0.92 mm.

Figure 6A:
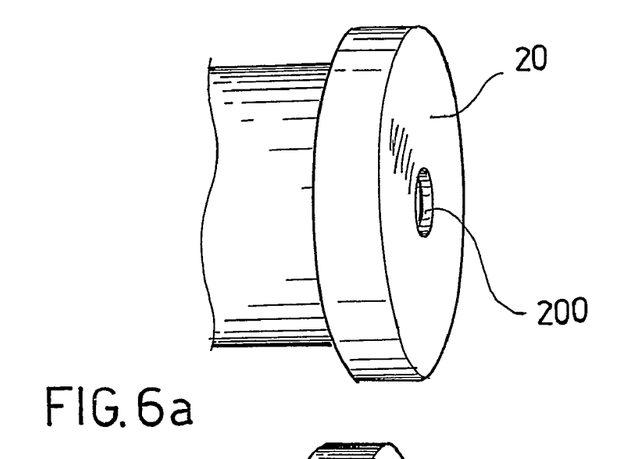
FIGS. 6*a* to 6*d* are schematic views of four sequential steps of an embodiment of the method according to the invention.
Figure 6B:
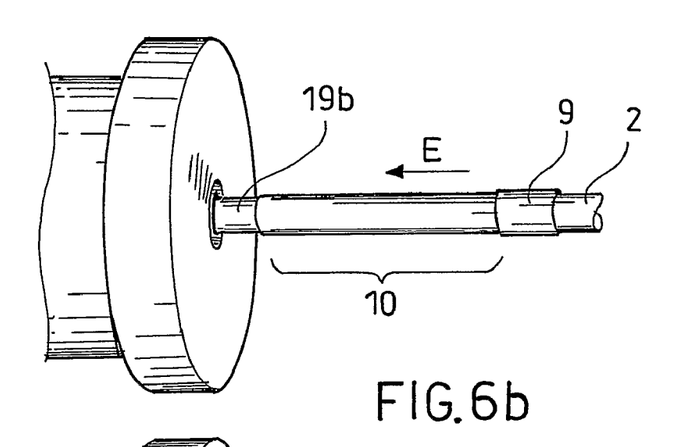
Figure 6C:
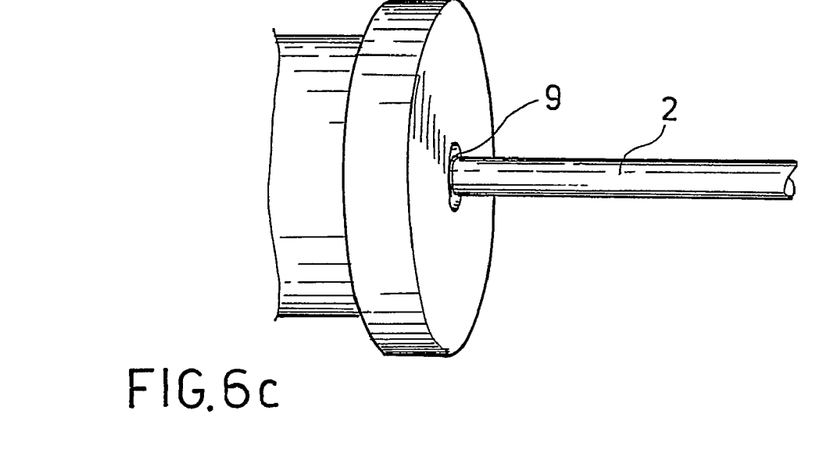
Figure 6D:
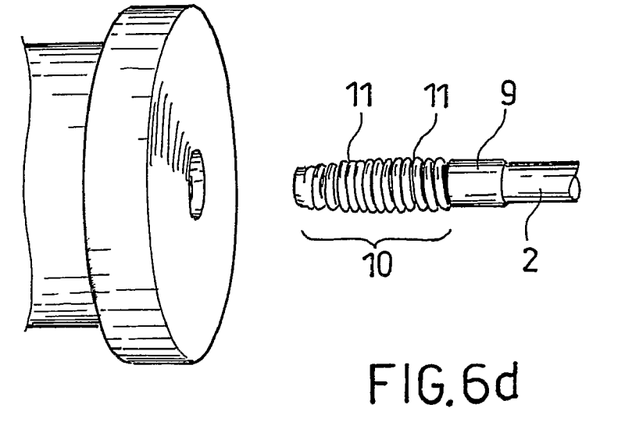
Figure 7:
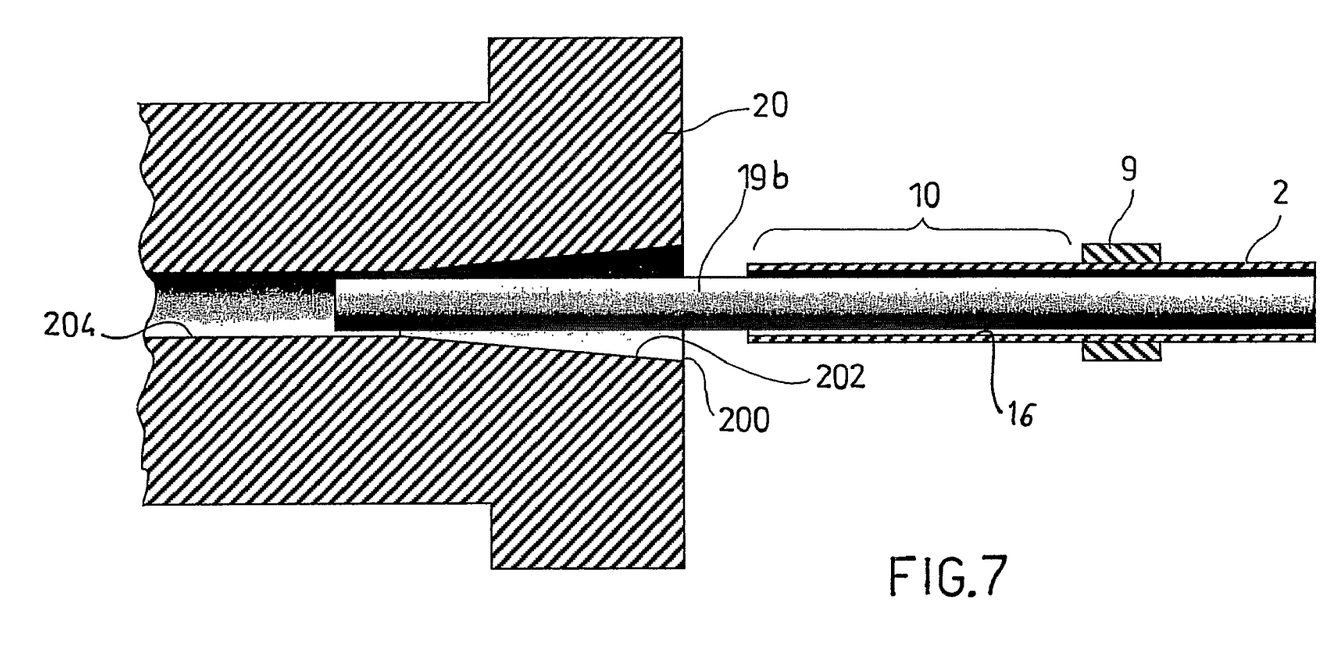
FIG. 7 is a view of a peripheral section of FIG. 6*b*.

In accordance with a preferred embodiment, at this point the second stylet 19*b* and the distal flap 10 of main tube 2 supported thereby are inserted in a second ferrule 20 preferably heated and countersunk. The diameter of the second ferrule 20 hole is, in a first length 202 immediately adjacent to mouth 200, greater than the outer diameter of distal flap 10 of main tube 2. On the other hand, in a second deeper length 204 the ferrule hole diameter is such to allow the insertion of the second stylet 19*b* but not of the distal flap 10. Preferably, the transition from the first length 202 diameter to the second length 204 diameter of the ferrule hole 20 takes place by a countersink. By forcing the main tube 2 inside the second ferrule 20 (arrow E in FIG. 6*b*), the tube wall is subjected to an axial compression stress. By further forcing the main tube 2 inside the second ferrule 20, the compression stress increases until it creates a local phenomenon of wall instability (buckling). The deformation resulting from instability gives rise to the relieves 11. In fact, the tube wall becoming unstable due to the axial compression load becomes buckled. The outside diameter of the resulting bucklings are limited both internally by the wall of stylet 19*b* and externally by the wall of the second ferrule 20.

Due to the presence of a countersink at the mouth of second ferrule 20 the relieves 11 will not be all equal to one another, and their outside diameter will increase in the proximal direction (from right to left in FIG. 2).

If the second ferrule 20 is heated, thus altering the mechanical characteristics of the material constituting the tube 2, the instability resulting from axial compression load will be more easily achieved.

In accordance with an embodiment, the main development direction of reliefs 11 is transversal to the tube axis.

In accordance with a preferred embodiment, the main development direction of reliefs 11 is perpendicular to the tube axis.

Thereby, an optimum flexibility of the tube distal flap is obtained, because the reliefs perpendicular to the axis do not contribute in any way to stiffen it in a flexural manner.

A similar method can be used to form a relief which gives origin to the shoulder 7 for the first marker 8. In other words, this relief may consist of a buckling caused by local instability due to an axial compression load of the main tube 2 wall.

As an example, again it may be considered a distal flap 10 of main tube 2 made of poly-ether ether ketone (PEEK). It may be assumed that the outer diameter of the distal flap 10 has been reduced to 1.1 mm from a start diameter of the tube 2 of 1.23 mm. In this case, the diameter of the second length 204 of ferrule 20 can be 1 mm and the countersink can be of about 10°. Furthermore, the ferrule 20 can be heated up to a temperature of about 170° C.

Once the reliefs 11 have been formed, the method provides for the distal flap 10 of tube 2 to be inserted, while still being supported by a stylet, in a mould shaped as the tapered portion 12. A plastic material in the fluid state is injected by a known technique which forms the tapered portion 12 and forms a plurality of notches 13 therein, which are exactly complementary to reliefs 11, and if present, to second marker 9. Furthermore, in its polymerization step, this plastic material adheres to the outer surface of tube 2.

Accordingly, it is understood that the joint between the main tube 2 and the tapered portion 12 is not only of a chemical nature, but also of mechanical nature, i.e. resulting from the interpenetration among the reliefs 11 on tube 2 and the notches 13 in the tapered portion 12.

From what has been described above, it should be appreciated that the catheter and the method for making the same according to the invention overcome the drawbacks of the prior art.

It should be appreciated that the present invention provides an extremely flexible catheter. This characteristic enables the catheter itself to find its way through the blood vessels, which is often a tortuous path, in the simplest and less traumatic way for the patient.

This flexibility requirement is particularly met by the distal section and still more particularly by the catheter tip according to the invention.

Another requirement met by the catheter tip according to the invention is to fair the catheter front profile of the minimum diameter, for example that of the lumen with a guide wire running therein, to the maximum diameter found in the distal section, for example that of the sheath holding a stent which can be loaded on the catheter in its state of maximum radial collapse.

A further requirement met by the catheter tip according to the invention is to ensure that the flexibility of the distal end in the proximal direction will change as evenly as possible.

A still further requirement met by the catheter and the tip thereof is to ensure the adherence of the main tube 2 to the tapered portion, also in most severe usage conditions, to prevent them to fall apart.

It is also understood from what has been discussed above that the need is satisfied to obtain such a catheter by means of a simple method which does not require expensive technologies and ensures an optimum result by limiting the risk of errors.

To the preferred embodiments of the catheter and the method for making the same described above, those skilled in the art, aiming at satisfying contingent and specific needs, may carry out a number of modifications, variants and replacements of elements with others functionally equivalent, without departing from the scope of the claims below.

What is claimed is:

1. A catheter comprising
a main tube (2) having a proximal end and a distal end,
said distal end having a flexible portion (10) extending along an axis and
a tapered tip (12) connected coaxially to said flexible portion (10),
said flexible portion (10) comprising a plurality of external reliefs (11) arranged on planes transverse to said axis,
said tapered tip (12) comprising a plurality of internal grooves (13) complementary to said reliefs (11) and engaging said reliefs to retain the tip on the main tube,
said tip having a larger proximal end and a smaller distal end,
wherein said reliefs have an outside diameter which increases in a proximal direction from the distal end to the proximal end.

2. A catheter according to claim 1 wherein said reliefs (11) are arranged on planes perpendicular to said axis.

3. A catheter according to claim 1 wherein said reliefs (11) comprise corrugations of the tube (2) wall.

4. A catheter according to claim 1 further comprising a radiopaque marker (9).

5. A catheter according to claim 4 wherein said tapered portion (12) further comprises a notch complementary to said radiopaque marker (9).

6. A catheter according to claim 1 wherein said tapered portion (12) comprises an apex port (14) for a guide wire to pass therethrough.

7. A catheter according to claim 6 wherein said tapered portion (12) comprises a distal section (120) suitable to fair the diameter of the apex port (14) with the outer diameter of a sheath (3).

8. A catheter according to claim 7 wherein said distal section (120) of said tapered portion (12) substantially has the shape of a truncated cone.

9. A catheter according to claim 1 wherein said tapered portion (12) comprises a proximal section (122) suitable to fair the diameter of the distal section (120) of said tapered portion (12) with the outer diameter of said main tube (2).

10. A catheter according to claim 9 wherein said proximal section (120) of said tapered portion (12) substantially has the shape of a truncated cone.

11. A catheter according to claim 9 wherein said proximal section (120) of said tapered portion (12) comprises a shoulder (17).

12. Distal section (5) of catheter (1) comprising a tip (15) according to claim 1 and a first marker (8) placed at a preset distance in the proximal direction from said tip (15).

13. Distal section (5) of catheter (1) according to claim 12 wherein said distance is preset based on the length of a stent loadable on said catheter (1).

14. Distal section (5) of catheter (1) according to claim 12 wherein said main tube (2) comprises a shoulder (7) against which said first marker (8) is in axial abutment.

15. Distal section (5) of catheter (1) according to claim 14 wherein said shoulder (7) comprises an abrupt change of the main tube (2) outer diameter.

16. Distal section (5) of catheter (1) according to claim 14 wherein said shoulder (7) comprises a buckling of the main tube (2) wall.

17. Distal section (5) of catheter (1) according to claim 14 wherein said shoulder (7) comprises a distal end of an intermediate tube (23) coaxially interposed between said main tube (2) and said sheath (3).

18. Distal section (5) of catheter (1) according to claim 12 wherein said first marker (8) is shaped such as to define in turn a shoulder.

19. Catheter (1) comprising a distal section (5) in accordance with claim 12.

20. Catheter (1) comprising a distal section (5) in accordance with claim 17 wherein said intermediate tube (23) comprises a reinforcement (25) made of a material stiffer than the material composing the wall of said intermediate wall (23).

21. Catheter (1) in accordance with claim 20 wherein said reinforcement comprises a metal coil (25).

22. Method for making a catheter in accordance with claim 1, comprising the steps of:
providing a main tube (2) of said catheter (1),
providing a distal flap (10) of said main tube (2) defining an axis;
providing on the outer surface of said distal flap (10) a plurality of external reliefs (11) on transverse planes to said axis;
overmolding coaxially to said distal flap (10) a tapered tip (12) having a distal end and a proximal end,
wherein said reliefs have an outside diameter which increases in a proximal direction from the distal end to the proximal end; and
providing in said tapered portion (12) a plurality of notches (13) complementary to said reliefs (11).

23. Method in accordance with claim 22, wherein said step of providing said plurality of reliefs (11) on said distal flap (10), comprises in turn the steps of:
loading the wall of said distal flap (10) of said main tube (2) by axial compression;
induce a phenomenon of local instability suitable to cause on said distal flap (10) a plurality of bucklings.

24. Method in accordance with claim 22, further comprising the step of heating said distal flap (10) of said main tube (2).

25. Method in accordance with claim 22, further comprising the step of supporting said distal flap (10) of said main tube (2) with a rigid stylet (19b).

26. Method in accordance with claim 23, wherein said step of providing said plurality of reliefs (11) on said distal flap (10) comprises a step of using a ferrule.

27. Method in accordance with claim 23, wherein said step of providing said plurality of reliefs (11) on said distal flap (10) comprises a step of using a heated ferrule.

28. Method in accordance with claim 23, wherein said step of providing said plurality of reliefs (11) on said distal flap (10) comprises a step of using a countersunk ferrule.

29. Method for making a distal section (5) of a catheter (1) in accordance with claim 12, comprising the steps of:
providing a tip (15) by
providing a main tube of said catheter,
providing a distal flap of said main tube defining an axis,
providing on the outer surface of said distal flap a plurality of reliefs on transverse planes to said axis, overmolding coaxially to said distal flap a tapered tip having a distal end and a proximal end,
providing in said tapered portion a plurality of notches complementary to said reliefs, and
providing a first marker (8) to a predefined distance in the proximal direction from said tip (15),
wherein said reliefs have an outside diameter which increases in a direction from the distal end to the proximal end.

30. Method in accordance with claim 29, wherein said distance is predefined based on the length of a stent loadable on said catheter (1).

31. Method in accordance with claim 29, comprising the steps of:
providing a shoulder (7) on said main tube (2);
axially abutting a first marker (8) against said shoulder (7).

32. Method in accordance with claim 29, wherein said step of providing a shoulder (7) on said main tube (2) comprises the step of forcing said distal section (5) of said main tube (2) inside a first heated ferrule (18) with a slightly smaller diameter than the outer diameter of said main tube (2).

33. Method in accordance with claim 29, wherein said step of providing a shoulder (7) on said main tube (2) comprises steps of:
loading by axial compression the wall of said main tube (2) by axial compression;
inducing a phenomenon of local instability suitable to cause a buckling on said wall.

34. Method in accordance with claim 29, wherein said step of providing on said main tube (2) a shoulder (7) comprises the step of providing the distal end of an intermediate tube (23) coaxially interposed between said main tube (2) and said sheath (3).

* * * * *